(12) United States Patent
Liu et al.

(10) Patent No.: US 10,719,014 B2
(45) Date of Patent: Jul. 21, 2020

(54) PHOTORESISTS COMPRISING AMIDE COMPONENT

(71) Applicant: Rohm and Haas Electronic Materials LLC, Marlborough, MA (US)

(72) Inventors: Cong Liu, Shrewsbury, MA (US); Chunyi Wu, Shrewsbury, MA (US); Gerhard Pohlers, Needham, MA (US); Gregory P. Prokopowicz, Worcester, MA (US); Mingqi Li, Shrewsbury, MA (US); Cheng-Bai Xu, Southborough, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 0 days.

(21) Appl. No.: 13/926,764

(22) Filed: Jun. 25, 2013

(65) Prior Publication Data
US 2013/0344439 A1 Dec. 26, 2013

Related U.S. Application Data

(60) Provisional application No. 61/664,098, filed on Jun. 25, 2012.

(51) Int. Cl.
| | |
|---|---|
| *G03F 7/004* | (2006.01) |
| *G03F 7/038* | (2006.01) |
| *G03F 7/20* | (2006.01) |
| *G03F 7/039* | (2006.01) |
| *C08F 220/52* | (2006.01) |
| *C07C 233/16* | (2006.01) |
| *C07C 233/02* | (2006.01) |
| *C08F 220/56* | (2006.01) |
| *C07C 233/00* | (2006.01) |
| *C07C 233/01* | (2006.01) |
| *C08F 220/58* | (2006.01) |

(52) U.S. Cl.
CPC ............ *G03F 7/004* (2013.01); *C07C 233/00* (2013.01); *C07C 233/01* (2013.01); *C07C 233/02* (2013.01); *C07C 233/16* (2013.01); *C08F 220/52* (2013.01); *C08F 220/56* (2013.01); *C08F 220/58* (2013.01); *G03F 7/0382* (2013.01); *G03F 7/0397* (2013.01); *G03F 7/2041* (2013.01)

(58) Field of Classification Search
CPC ......... G03F 7/00; G03F 7/004; C07C 233/00; C07C 233/01; C07C 233/02; C07C 233/16; C08F 220/52; C08F 220/56; C08F 220/58
USPC ........ 430/270.1, 913, 927, 283.1; 526/303.1, 526/304, 305, 307.2; 544/35, 61
See application file for complete search history.

(56) References Cited

U.S. PATENT DOCUMENTS

| | | | | |
|---|---|---|---|---|
| 2,170,845 | A * | 8/1939 | Woodhouse | 106/170.44 |
| 2,259,466 | A * | 10/1941 | Harris et al. | 514/788 |
| 2,411,957 | A * | 12/1946 | Keiser et al. | 554/63 |
| 2,848,335 | A * | 8/1958 | Bell et al. | 426/544 |
| 2,870,091 | A * | 1/1959 | Tomlinson | 510/337 |
| 3,108,081 | A * | 10/1963 | Gleim et al. | 502/163 |
| 3,321,455 | A * | 5/1967 | Combs et al. | 428/220 |
| 3,365,437 | A * | 1/1968 | Marra et al. | 524/223 |
| 3,365,452 | A * | 1/1968 | Weilenreuther et al. | 544/217 |
| 3,422,141 | A * | 1/1969 | Carlsson et al. | 564/170 |
| 3,898,279 | A * | 8/1975 | Hoke | 564/205 |
| 3,932,324 | A * | 1/1976 | Stretanski | 524/223 |
| 4,070,484 | A * | 1/1978 | Harita et al. | 514/563 |
| 4,115,637 | A * | 9/1978 | Cenci et al. | 525/328.2 |
| 4,138,541 | A * | 2/1979 | Cenci et al. | 524/233 |
| 4,542,090 | A * | 9/1985 | Lewis | 430/396 |
| 4,929,534 | A * | 5/1990 | Stephani et al. | 430/191 |
| 5,264,485 | A * | 11/1993 | Muller et al. | 524/724 |
| 5,322,898 | A * | 6/1994 | Chaudhuri et al. | 525/183 |
| 5,646,318 | A * | 7/1997 | Dery et al. | 554/69 |
| 5,750,680 | A * | 5/1998 | Kim et al. | 540/200 |
| 6,031,113 | A * | 2/2000 | Nishikawa | 548/544 |
| 6,051,678 | A * | 4/2000 | Kim et al. | 528/323 |
| 6,183,934 | B1 | 2/2001 | Kawamonzen | |
| 6,486,058 | B1 | 11/2002 | Chun | |
| 6,607,870 | B2 | 8/2003 | Thackeray et al. | |
| 6,767,479 | B1 * | 7/2004 | Rossi et al. | 252/182.26 |
| 7,030,272 | B2 * | 4/2006 | Kaplan et al. | 564/186 |
| 7,326,516 | B2 * | 2/2008 | Nishiyama et al. | 430/270.1 |
| 7,745,077 | B2 * | 6/2010 | Thiyagarajan et al. | 430/14 |

(Continued)

FOREIGN PATENT DOCUMENTS

| | | | |
|---|---|---|---|
| GB | 2320500 | A * | 6/1998 |
| JP | 01009973 | A * | 1/1989 |

(Continued)

OTHER PUBLICATIONS

English Language Summary of Office Action issued in counterpart Taiwan Application No. 103-2(6) 01271-10321138380, dated Aug. 20, 2014 (3 Pages).
English Language Summary of First Office Action issued in counterpart Chinese Application No. 201310364299.4, Dispatch Date: Jun. 3, 2015 (7 Pages).
English Language Summary of Second Office Action issued in counterpart Chinese Application No. 201310364299.4, Dispatch Date: Apr. 14, 2016 (5 Pages).
English Language Summary of Office Action issued in counterpart Japanese Application No. 2013-131756 (5 Pages).

(Continued)

*Primary Examiner* — Amanda C. Walke
(74) *Attorney, Agent, or Firm* — Mintz Levin Cohn Ferris Glovsky and Popeo, P.C.; Peter F. Corless

(57) ABSTRACT

New photoresist compositions are provided that comprise a component that comprises an amide group and multiple hydroxyl groups. Preferred photoresists of the invention may comprise a resin with photoacid-labile groups; a photoacid generator compound; and an amide component with multiple hydroxyl groups that can function to decrease undesired photogenerated-acid diffusion out of unexposed regions of a photoresist coating layer.

18 Claims, No Drawings

(56) References Cited

U.S. PATENT DOCUMENTS

| | | | |
|---|---|---|---|
| 7,830,272 B2 * | 11/2010 | Thurmond et al. | 340/870.02 |
| 7,923,200 B2 * | 4/2011 | Thiyagarajan et al. | 430/313 |
| 8,124,318 B2 * | 2/2012 | Sugeta et al. | 430/273.1 |
| 8,507,175 B2 * | 8/2013 | Hatakeyama et al. | 430/270.1 |
| 8,741,537 B2 * | 6/2014 | Kanda | 430/270.1 |
| 8,758,978 B2 * | 6/2014 | Satou et al. | 430/270.1 |
| 2006/0210922 A1 * | 9/2006 | Nishiyama | 430/270.1 |
| 2006/0287207 A1 | 12/2006 | Park et al. | |
| 2007/0010651 A1 * | 1/2007 | Finch et al. | 528/310 |
| 2008/0020289 A1 * | 1/2008 | Hatakeyama et al. | 430/4 |
| 2008/0090179 A1 * | 4/2008 | Takeda et al. | 430/286.1 |
| 2009/0156080 A1 * | 6/2009 | Finch et al. | 442/417 |
| 2010/0266957 A1 * | 10/2010 | Harada et al. | 430/285.1 |
| 2011/0223535 A1 | 9/2011 | Liu et al. | |
| 2012/0070778 A1 * | 3/2012 | Ichikawa et al. | 430/270.1 |
| 2012/0077120 A1 | 3/2012 | Prokopowicz et al. | |
| 2012/0136482 A1 * | 5/2012 | Samples et al. | 700/269 |
| 2012/0171612 A1 * | 7/2012 | Satou et al. | 430/270.1 |
| 2012/0181240 A1 * | 7/2012 | Crowley | 211/26 |
| 2012/0219919 A1 * | 8/2012 | Thiyagarajan et al. | 430/331 |
| 2013/0123505 A1 * | 5/2013 | Tomokawa et al. | 546/317 |
| 2014/0038106 A1 * | 2/2014 | Fukumoto et al. | 430/283.1 |

FOREIGN PATENT DOCUMENTS

| | | | | |
|---|---|---|---|---|
| JP | 10182754 | A | * | 7/1998 |
| JP | 2000-338678 | A | | 12/2000 |
| JP | 2003-107705 | A | | 4/2003 |
| JP | 2003114526 | A | | 4/2003 |
| JP | 2006290790 | A | * | 10/2006 |
| JP | 2008174740 | A | * | 7/2008 |
| JP | 2009-144059 | A | | 7/2009 |
| JP | 2012-073612 | A | | 4/2012 |
| JP | 2012116965 | A | * | 6/2012 |
| JP | 2012197268 | A | * | 10/2012 |
| KR | 20120028291 | A | | 3/2012 |
| WO | 2005003198 | A1 | | 1/2005 |

OTHER PUBLICATIONS

English Language Summary of Office Action dated Nov. 21, 2019 in counterpart Korean Application No. 10-2013-0073103 (11 Pages).

English Language Summary of Office Action dated Feb. 24, 2018 issued in counterpart Chinese Application No. 2013103642994 (4 Pages).

* cited by examiner

PHOTORESISTS COMPRISING AMIDE COMPONENT

This application claims the benefit of priority under 35 U.S.C. § 119(e) to U.S. Provisional Application No. 61/664,098, filed Jun. 25, 2012, the entire contents of which application are incorporated herein by reference.

This invention relates to photoresist compositions that comprise an amide component that comprises two or more hydroxy groups. Preferred photoresists of the invention may comprise a resin with photoacid-labile groups; a photoacid generator compound; and an amide component with multiple hydroxyl groups that can function to decrease undesired photogenerated-acid diffusion out of unexposed regions of a photoresist coating layer.

Photoresists are photosensitive films for transfer of images to a substrate. They form negative or positive images. After coating a photoresist on a substrate, the coating is exposed through a patterned photomask to a source of activating energy, such as ultraviolet light, to form a latent image in the photoresist coating. The photomask has areas opaque and transparent to activating radiation that define an image desired to be transferred to the underlying substrate.

Known photoresists can provide features having resolution and size sufficient for many existing commercial applications. However for many other applications, the need exists for new photoresists that can provide highly resolved images of sub-quarter-micron (<0.25 μm) dimension.

Various attempts have been made to alter the make-up of photoresist compositions to improve performance of functional properties. Among other things, a variety of basic compounds have been reported for use in photoresist compositions. See, e.g., U.S. Pat. Nos. 6,486,058, 6,607,870 and 7,379,548, as well as Japanese published patents JP 1103086 and 1231538. See also U.S. 2011/0223535 and US 2012/0077120.

The present invention provides photoresist compositions comprising a resin, a photoacid generator compound (photoacid generator or "PAG"), and an amide-containing compound that comprises i) an amide group; and ii) two or more hydroxyl groups.

Preferred amide compounds can function as a photoacid diffusion control agent during lithographic processing of a photoresist composition coating layer. Such diffusion control may be suitable assessed by improved resolution of a developed relief image of a resist that comprises the amide compound relative to the relief image of an otherwise comparable resist that does not contain the amide compound.

Preferred amide compounds also may comprise greater than two hydroxyl groups, such as 3, 4, 5, 6 or more hydroxyl groups. Typically preferred amide compounds may comprise 2, 3, or 4 hydroxyl groups.

Preferred amide compounds may comprise hydroxyl group substitution in a variety of configurations, including primary and/or secondary alcohol moieties. Tertiary hydroxyl moieties also may be present.

Preferred amide compounds include those that contain a single amide moiety (i.e. a total one of one amide moiety). In certain others embodiments, an amide compound for use in a photoresist composition will contain more than one amide group.

Preferred amide compounds also include those that do not contain a carbamate group. Additional preferred amide compounds include those that do not contain a photoacid-labile group, such as a photoacid-labile ester, carbamate and/or acetal group.

In certain aspects, an amide compound for use in a photoresist composition as disclosed herein will contain a single amide moiety, will not contain a carbamate group, and/or will not contain a photoacid-labile group.

Preferred amide compounds also may comprise other moieties in addition to hydroxyl, such as halo (F,Cl, Br, and/or I, particularly F); cyano, carboxyl (—COOH), ester (e.g. —COOR where R is $C_{1-12}$alkyl). Polar functional groups that can complex with photogenerated acid, such as cyano and carboxy are often particularly preferred.

In certain preferred aspects, an amide compound corresponds to the following Formula I:

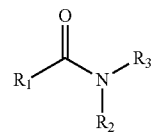

I wherein R1, R2 and R3 are each independently hydrogen or a non-hydrogen substituent; and R1, R2 and R3 together comprise two or more hydroxyl groups.

In that Formula (I), in certain preferred aspects, R1 is a non-hydrogen substituent and at least one of R2 and R3 are non-hydrogen substituents. In other certain preferred aspects, R1 is optionally substituted alkyl, and R2 and R3 are independently hydrogen or optionally substituted alkyl. In yet other certain preferred aspects, R1, R2 and R3 are each the same or different optionally substituted alkyl. In further preferred aspects, R1 and R2 are taken together to provide an optionally substituted lactam group, such as a lactam group having 4, 5, 6 or 7 ring members. In yet further preferred aspects, R2 and R3 are taken together to provide a ring structure, such as a ring group having 4, 5, 6 or 7 ring members.

Photoresists of the invention may be either positive-acting or negative-acting, and preferably are positive-acting.

In a preferred aspect, photoresists of the invention used for short-wavelength imaging applications, such as 193 nm imaging.

Particularly preferred photoresists of the invention may be used in immersion lithography applications.

We have found that use of a present amide compound in a photoresist composition, including chemically-amplified photoresist compositions, can significantly enhance resolution of a relief image (for example, fine lines) of the resist. In particular, we have found that an amide compound as disclosed herein imparts significantly enhanced lithographic results, including relative to a comparable photoresist that is otherwise identical to the photoresist that instead contains a different basic additive. Use of an amide compound as disclosed herein also can provide improved shelf life to photoresists containing the compound.

Preferred amide compounds of the invention for use in photoresists may be polymeric or non-polymeric, with non-polymeric amide compounds preferred for many applications. Preferred amide compounds have relatively low molecular weight, for example, a molecular weight of less than or equal to 3000, more preferably ≤2500, ≤2000, ≤1500, ≤1000, ≤800 or even more preferably ≤500.

Specifically preferred amide compounds for use in photoresist compositions as disclosed herein include the following:
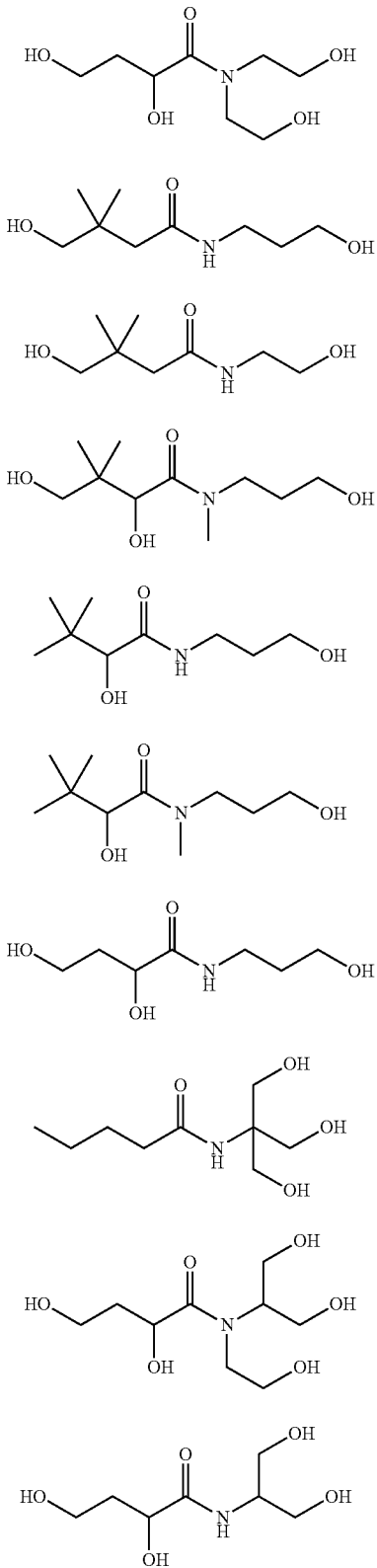
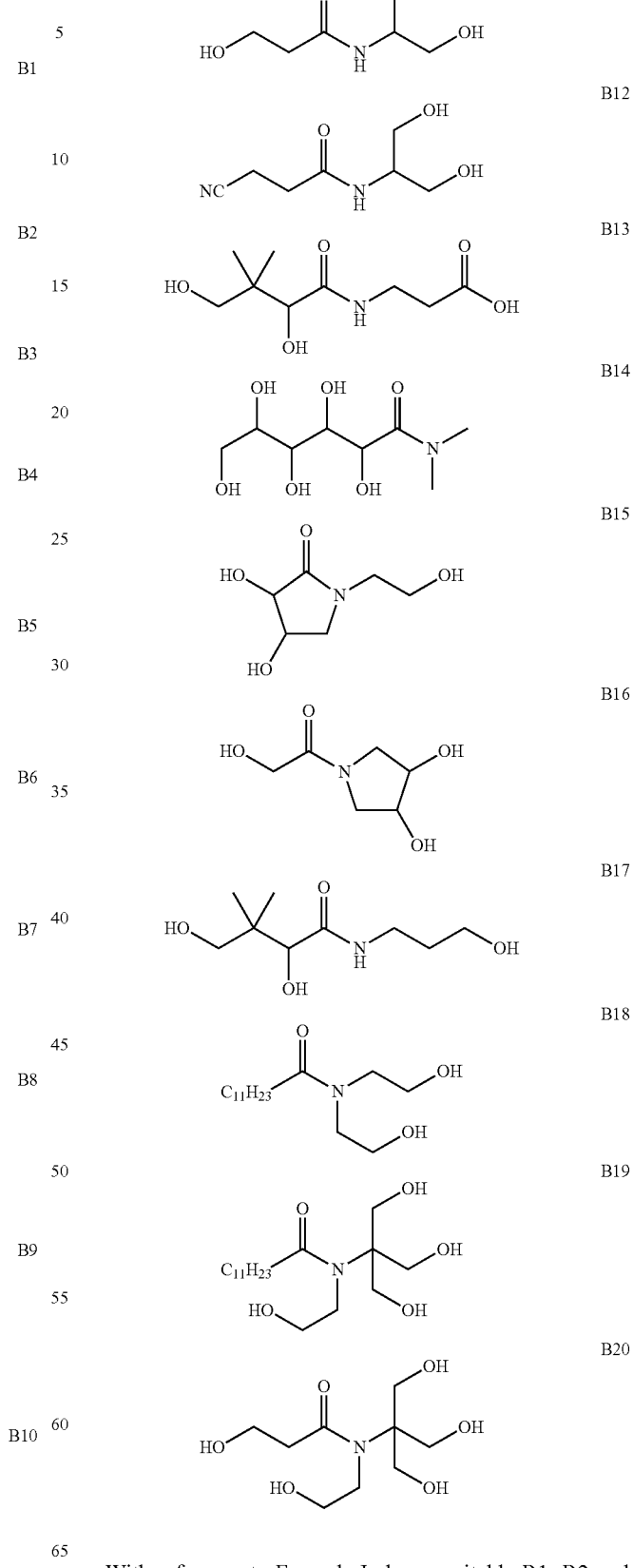
With reference to Formula I above, suitable R1, R2 and R3 moieties include those independently chosen from H, optionally substituted $(C_1-C_{30})$alkyl, and optionally substituted carbocyclic aryl such as phenyl, or as discussed above R1 and R2 or R2 and R3 may be taken together along with the atoms to which they are attached to form an optionally substituted 4- to 12-membered heterocyclic ring.

In certain preferred aspects, R1, R2 and R3 may be independently chosen from H and optionally substituted $(C_1-C_{30})$alkyl.

As stated, R1, R2 and R3 may be moieties that are optionally substituted. Substituted moieties are suitably substituted at one or more available positions by e.g. carboxyl (—$CO_2H$), carboxy$(C_1-C_{30})$alkyl, $(C_1-C_{30})$alkoxy, sulfonyl, sulfonic acid, sulfonate ester, cyano, halo, and keto. Preferred substituent groups are carboxyl, carboxy$(C_1-C_{10})$alkyl, $(C_1-C_{10})$alkoxy, sulfonyl, sulfonic acid, sulfonate ester, cyano, halo, and keto; and more preferably carboxyl, carboxy$(C_1-C_8)$alkyl, $(C_1-C_8)$alkoxy, sulfonyl, sulfonic acid, sulfonate ester, cyano, halo, and keto. Preferred ester groups (carboxyalkyl) are carboxy$(C_1-C_6)$alkyl. Preferred alkoxy groups are $(C_1-C_6)$alkoxy, and more preferably $(C_1-C_5)$alkoxy. By "substituted," it is meant that one or more hydrogens on e.g. a carbon atom of the amide compound is replaced with one or more of the above substituent groups. A mixture of such substituent groups may be used. The presence of such substituent groups may impart desired solubility to the amide compound, or may be used to tailor the quenching ability of the amide compound.

When R1 and R2 or R2 and R3 are taken together along with the atoms to which they are attached to form a heterocyclic ring, they may form a single heterocyclic ring, or multiple rings which may be used or spirocyclic. It is preferred that when R1 and R2 or R2 and R3 are taken together along with the atoms to which they are attached that an optionally substituted 4- or 5- to 10-membered ring is formed, and more preferably an optionally substituted 5- to 8-membered ring, and even more preferably an optionally substituted 5 to 6-membered ring. It will be appreciated by those skilled in the art that a lactam is formed when R1 and R2 are taken together along with the atoms to which they are attached to form a ring.

Amide compounds useful in the present invention are generally commercially available or can be readily synthesized.

Preferably, amide compounds of the invention are used in positive-acting or negative-acting chemically amplified photoresists, i.e. negative-acting resist compositions which undergo a photoacid-promoted crosslinking reaction to render exposed regions of a coating layer of the resist less developer soluble than unexposed regions, and positive-acting resist compositions which undergo a photoacid-promoted deprotection reaction of acid labile groups of one or more composition components to render exposed regions of a coating layer of the resist more soluble in an aqueous developer than unexposed regions. Ester groups that contain a tertiary non-cyclic alkyl carbon or a tertiary alicyclic carbon covalently linked to the carboxyl oxygen of the ester are generally preferred photoacid-labile groups of resins employed in photoresists of the invention. Acetal groups also are suitable photoacid-labile groups.

Photoresists of the invention typically comprise a resin binder (polymer), a photoactive component such as a photoacid generator, and an amide compound as disclosed herein. Preferably the resin binder has functional groups that impart alkaline aqueous developability to the photoresist composition. For example, preferred are resin binders that comprise polar functional groups such as hydroxyl or carboxylate. Preferably the resin binder is used in a resist composition in an amount sufficient to render the resist developable with an aqueous alkaline solution.

Preferred imaging wavelengths of the photoresists of the invention include sub-300 nm wavelengths, such as 248 nm, and more preferably sub-200 nm wavelengths, such as 193 nm and EUV.

Particularly preferred photoresists of the invention may be used in immersion lithography applications. See, for example, U.S. Pat. No. 7,968,268 to Rohm and Haas Electronic Materials for a discussion of preferred immersion lithography photoresists and methods. Preferred photoresists for use in immersion application may comprise a resin (which may be fluorinated and/or have photoacid-labile groups) that is separate (not covalently linked) and distinct from a primary resin that has photoacid-labile groups. Thus, the present invention includes in preferred aspects photoresists that comprise: 1) a first resin with photoacid-labile groups; 2) one or more photoacid generator compounds; 3) a second resin that is separate and distinct from the first resin, the second resin may be fluorinated and/or have photoacid-acid groups; and 4) one or more amide compounds as disclosed herein.

Particularly preferred photoresists of the invention contain an imaging-effective amount of one or more PAGs and one or more amide compounds as disclosed herein and a resin that is selected from the group of:

1) a phenolic resin that contains acid-labile groups that can provide a chemically amplified positive resist particularly suitable for imaging at 248 nm Particularly preferred resins of this class include: i) polymers that contain polymerized units of a vinyl phenol and an alkyl(meth)acrylate, where the polymerized alkyl(meth)acrylate units can undergo a deblocking reaction in the presence of photoacid. Exemplary alkyl(meth)acrylates that can undergo a photoacid-induced deblocking reaction include e.g. t-butyl acrylate, t-butyl methacrylate, methyladamantyl acrylate, methyl adamantyl methacrylate, and other non-cyclic alkyl and alicyclic(meth)acrylates that can undergo a photoacid-induced reaction, such as polymers in U.S. Pat. Nos. 6,042,997 and 5,492,793, incorporated herein by reference; ii) polymers that contain polymerized units of a vinyl phenol, an optionally substituted vinyl phenyl (e.g. styrene) that does not contain a hydroxy or carboxy ring substituent, and an alkyl(meth)acrylate such as those deblocking groups described with polymers i) above, such as polymers described in U.S. Pat. No. 6,042,997, incorporated herein by reference; and iii) polymers that contain repeat units that comprise an acetal or ketal moiety that will react with photoacid, and optionally aromatic repeat units such as phenyl or phenolic groups;

2) a resin that is substantially or completely free of phenyl groups that can provide a chemically amplified positive resist particularly suitable for imaging at sub-200 nm wavelengths such as 193 nm Particularly preferred resins of this class include: i) polymers that contain polymerized units of a non-aromatic cyclic olefin (endocyclic double bond) such as an optionally substituted norbornene, such as polymers described in U.S. Pat. No. 5,843,624; ii) polymers that contain alkyl(meth)acrylate units such as e.g. t-butyl acrylate, t-butyl methacrylate, methyladamantyl acrylate, methyl adamantyl methacrylate, and other non-cyclic alkyl and alicyclic(meth)acrylates; such polymers have been described in U.S. Pat. No. 6,057,083. Polymers of this type may contain in preferred aspects certain aromatic groups such as hydroxynaphthyl.

Preferred resins for use in photoresists to be imaged at sub-200 nm, such as at 193 nm, comprises units of two or more of the following general formulae (I), (II) and (III):

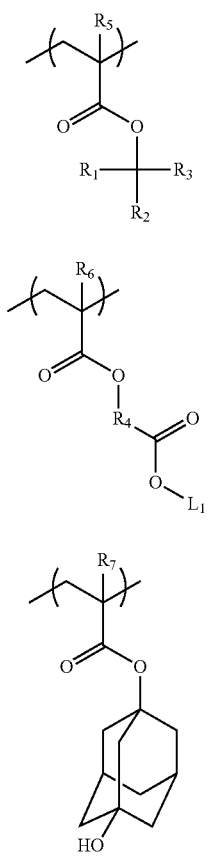

(I)

(II)

(III)

wherein: $R_1$, R2 and R3 are each optionally substituted $(C_1\text{-}C_{30})$alkyl group; $R_1$, $R_2$ and $R_3$ may connect to form a ring; $R_4$ is a $(C_1\text{-}C_3)$alkylene group; $L_1$ is a lactone group; and $R_5$, $R_6$ and $R_7$ are each hydrogen, fluorine, (C1-C4)alkyl and (C1-C4)fluoroalkyl.

The unit of general formula (I) includes an acid labile group that undergoes a photoacid-promoted deprotection reaction on exposure to activating radiation and heat treatment. This allows for a switch in polarity of the matrix polymer, leading to a change in solubility of the polymer and photoresist composition in an organic developer. Suitable monomers for forming units of formula (I) include, for example, the following:

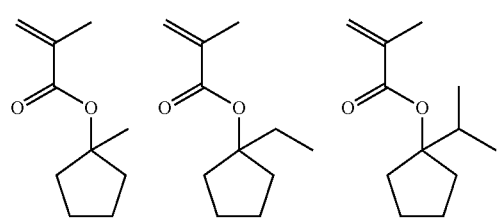

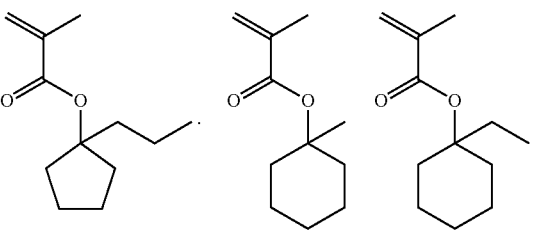

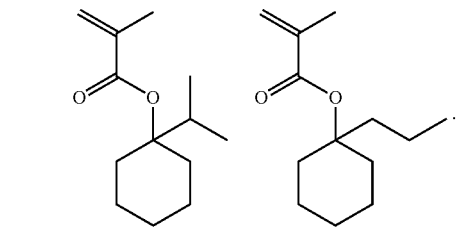

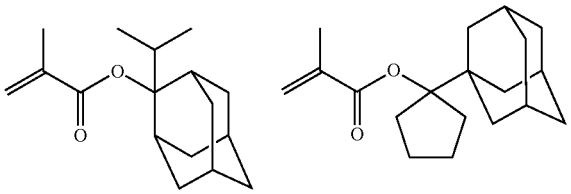

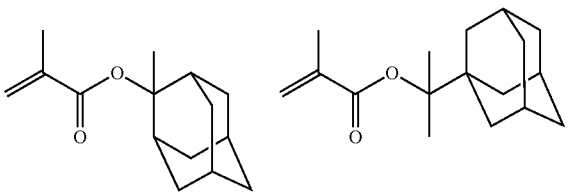

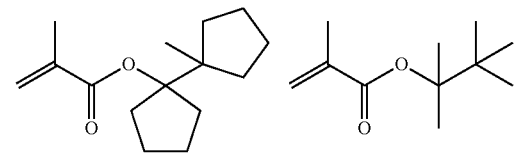

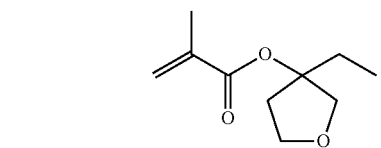

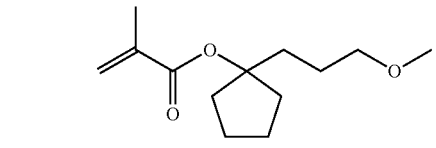

The unit of general formula (II) includes a lactone moiety effective to control the dissolution rate of the matrix polymer and photoresist composition. Suitable monomers for forming units of general formula (II) include, for example, the following:

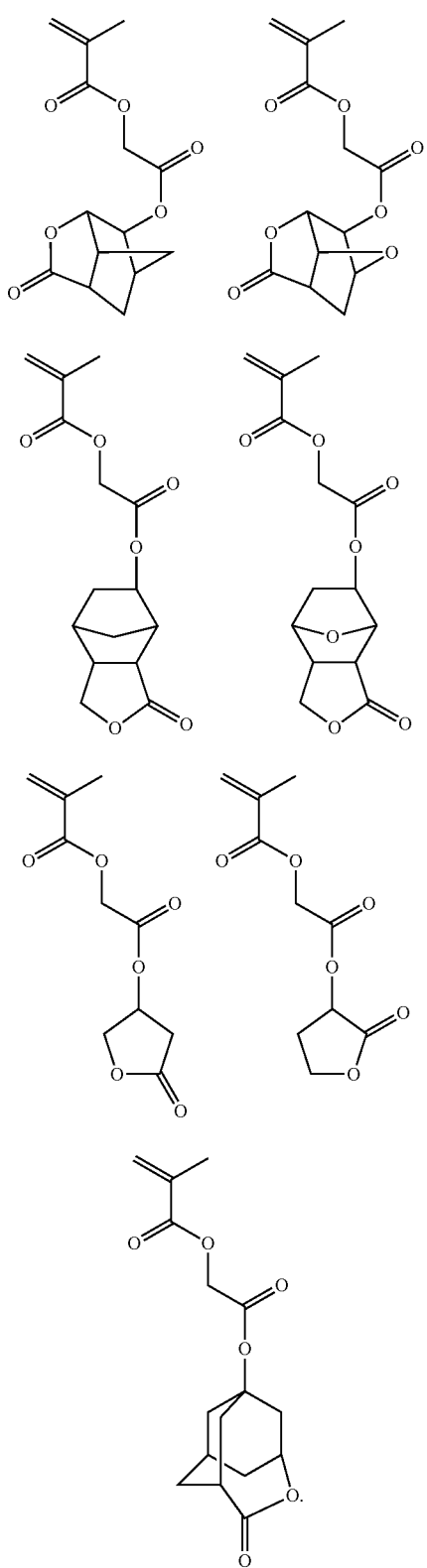

3-hydroxy-1-adamantyl methacrylate (HAMA) and preferably 3-hydroxy-1-adamantyl acrylate (HADA).

The resin can include one or more additional units of general formulae (I), (II) and/or (III) different from the first units. Where additional such units are present in the resin, they will preferably include an additional leaving group-containing unit of formula (I) and/or a lactone-containing unit of formula (II).

In addition to the polymerized units described above, the resin can include one or more additional units which are not of general formula (I), (II) or (III). For example, a particularly suitable lactone group-containing unit is of the following general formula (IV):

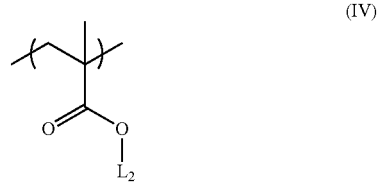

wherein: $L_2$ is a lactone group; and the unit of general formula (IV) is different from the unit of general formula (II). The following exemplary monomers are suitable for use in forming the additional lactone unit of general formula (IV):

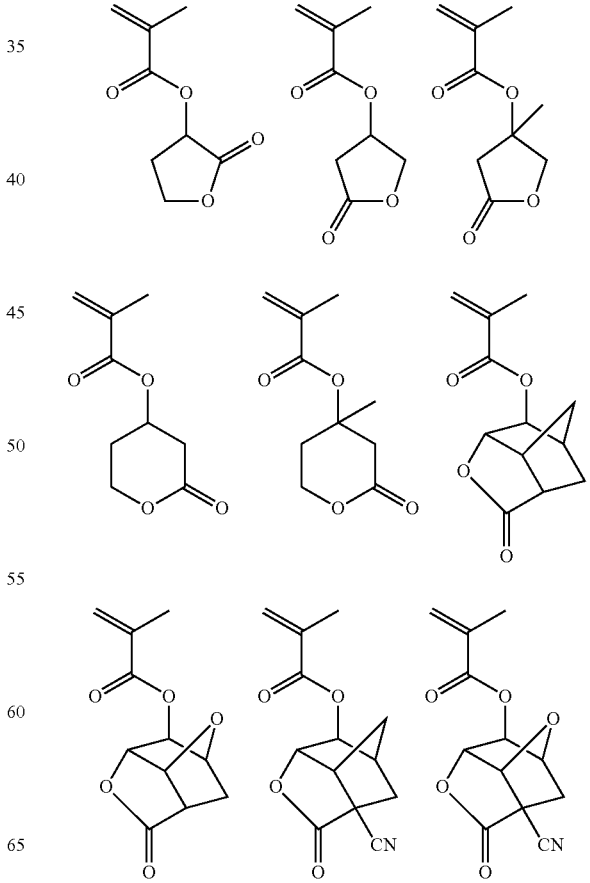

The unit of formula (III) provides a polar group, which enhances etch resistance of the resin and photoresist composition and provides additional means to control the dissolution rate of the resin and photoresist composition. Monomers for forming the unit of formula (III) include

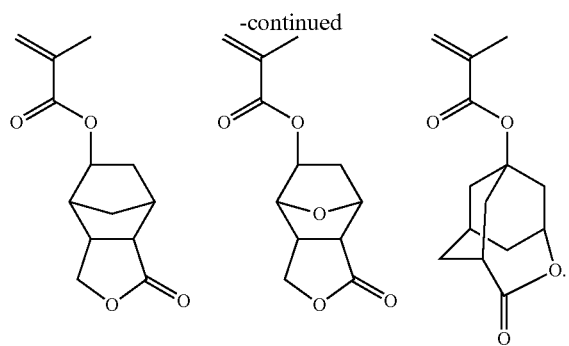

Preferably, $L_1$ in the unit of general formula (II) and $L_2$ in the unit of general formula (IV) are independently chosen from the following lactone groups:

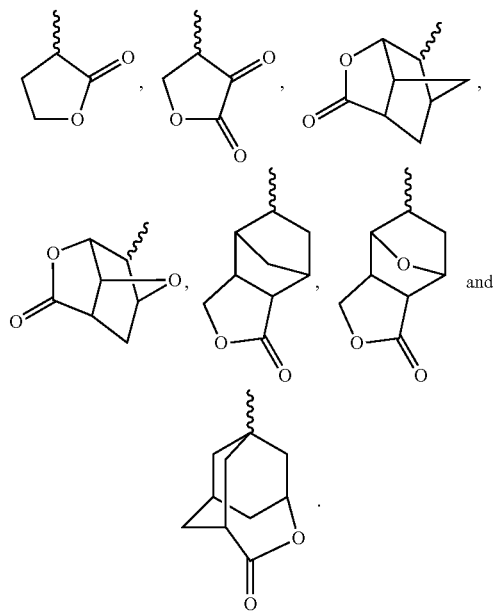

Typically, the additional units for the resin will include the same or similar polymerizable group as those used for the monomers used to form the units of general formula (I), (II) or (III), but may include other, different polymerizable groups in the same polymer backbone, such as those which contain polymerized units of vinyl or a non-aromatic cyclic olefin (endocyclic double bond) such as an optionally substituted norbornene. For imaging at sub-200 nm wavelengths such as 193 nm, the resin is typically substantially free (that is, less than 15 mole %) of phenyl, benzyl or other aromatic groups where such groups are highly absorbing of the radiation. Suitable additional monomeric units for the polymer include, for example, one or more of the following: monomeric units containing ethers, lactones or esters, such as 2-methyl-acrylic acid tetrahydro-furan-3-yl ester, 2-methyl-acrylic acid 2-oxo-tetrahydro-furan-3-yl ester, 2-methyl-acrylic acid 5-oxo-tetrahydro-furan-3-yl ester, 2-methyl-acrylic acid 3-oxo-4,10-dioxa-tricyclo[5.2.1.02,6]dec-8-yl ester, 2-methyl-acrylic acid 3-oxo-4-oxa-tricyclo[5.2.1.02,6]dec-8-yl ester, 2-methyl-acrylic acid 5-oxo-4-oxa-tricyclo[4.2.1.03,7] non-2-yloxycarbonylmethyl ester, acrylic acid 3-oxo-4-oxa-tricyclo[5.2.1.02,6]dec-8-yl ester, 2-methyl-acrylic acid 5-oxo-4-oxa-tricyclo[4.2.1.03,7] non-2-yl ester, and 2-methyl-acrylic acid tetrahydro-furan-3-yl ester; monomeric units having polar groups such as alcohols and fluorinated alcohols, such as 2-methyl-acrylic acid 3-hydroxy-adamantan-1-yl ester, 2-methyl-acrylic acid 2-hydroxy-ethyl ester, 6-vinyl-naphthalen-2-ol, 2-methyl-acrylic acid 3,5-dihydroxy-adamantan-1-yl ester, 2-methyl-acrylic acid 6-(3,3,3-trifluoro-2-hydroxy-2-trifluoromethyl-propyl)-bicyclo[2.2.1]hept-2-yl, and 2-bicyclo[2.2.1]hept-5-en-2-ylmethyl-1,1,1,3,3,3-hexafluoro-propan-2-ol; monomeric units having acid labile moieties, for example, ester groups that contain a tertiary non-cyclic alkyl carbon such as t-butyl, or a tertiary alicyclic carbon such as methyladamantyl or ethylfenchyl covalently linked to a carboxyl oxygen of an ester of the polymer, 2-methyl-acrylic acid 2-(1-ethoxy-ethoxy)-ethyl ester, 2-methyl-acrylic acid 2-ethoxymethoxy-ethyl ester, 2-methyl-acrylic acid 2-methoxymethoxy-ethyl ester, 2-(1-ethoxy-ethoxy)-6-vinyl-naphthalene, 2-ethoxymethoxy-6-vinyl-naphthalene, and 2-methoxymethoxy-6-vinyl-naphthalene. The additional units if used are typically present in the polymer in an amount of from 10 to 30 mol %.

Exemplary preferred resins include, for example, the following:

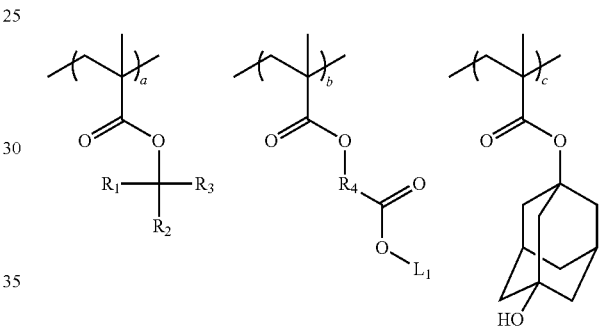

wherein: $0.3<a<0.7$; $0.3<b<0.6$; and $0.1<c<0.3$;

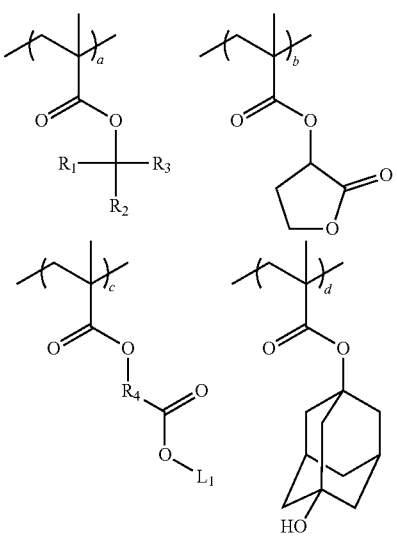

wherein: $0.3<a<0.7$; $0.1<b<0.4$; $0.1<c<0.4$, and $0.1<d<0.3$;

Blends of two or more resins can be used in the compositions of the invention. The resin is present in the resist composition in an amount sufficient to obtain a uniform coating of desired thickness. Typically, the resin is present in the composition in an amount of from 70 to 95 wt % based on total solids of the photoresist composition. Because of improved dissolution properties of the resin in organic developers, useful molecular weights for the resin are not limited to lower values, but cover a very broad range. For example, the weight average molecular weight $M_w$ of the polymers is typically less than 100,000, for example, from 5000 to 50,000, more typically from 6000 to 30,000 or from 7,000 to 25,000.

Suitable monomers used in forming the resins are commercially available and/or can be synthesized using known methods. The resins can readily be synthesized by persons skilled in the art using the monomers with known methods and other commercially available starting materials.

Photoresists of the invention also may comprise a single PAG or a mixture of distinct PAGs, typically a mixture of 2 or 3 different PAGs, more typically a mixture that consists of a total of 2 distinct PAGs. The photoresist composition comprises a photoacid generator (PAG) employed in an amount sufficient to generate a latent image in a coating layer of the composition upon exposure to activating radiation. For example, the photoacid generator will suitably be present in an amount of from 1 to 20 wt % based on total solids of the photoresist composition. Typically, lesser amounts of the PAG will be suitable for chemically amplified resists as compared with non-chemically amplified materials.

Suitable PAGs are known in the art of chemically amplified photoresists and include, for example: onium salts, for example, triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate; nitrobenzyl derivatives, for example, 2-nitrobenzyl-p-toluenesulfonate, 2,6-dinitrobenzyl-p-toluenesulfonate, and 2,4-dinitrobenzyl-p-toluenesulfonate; sulfonic acid esters, for example, 1,2,3-tris(methanesulfonyloxy)benzene, 1,2,3-tris(trifluoromethanesulfonyloxy)benzene, and 1,2,3-tris(p-toluenesulfonyloxy)benzene; diazomethane derivatives, for example, bis(benzenesulfonyl)diazomethane, bis(p-toluenesulfonyl)diazomethane; glyoxime derivatives, for example, bis-O-(p-toluenesulfonyl)-α-dimethylglyoxime, and bis-O-(n-butanesulfonyl)-α-dimethylglyoxime; sulfonic acid ester derivatives of an N-hydroxyimide compound, for example, N-hydroxysuccinimide methanesulfonic acid ester, N-hydroxysuccinimide trifluoromethanesulfonic acid ester; and halogen-containing triazine compounds, for example, 2-(4-methoxyphenyl)-4,6-bis(trichloromethyl)-1,3,5-triazine, and 2-(4-methoxynaphthyl)-4,6-bis(trichloromethyl)-1,3,5-triazine.

Photoresists of the invention comprise one or more amide compounds with multiple hydroxyl groups as disclosed herein in a wide amount range, such as from 0.005 to 15 wt %, based on the weight of the PAG, preferably from 0.01 to 15 wt %, and even more preferably from 0.01 to 10 wt %. The added amide component with multiple hydroxyl groups is suitably used in amounts of 0.01, 0.05, 0.1, 0.02, 0.3, 0.4, 0.5 or 1 to 10 or 15 wt % relative to the PAG, and more typically amounts of 0.01, 0.05, 0.1, 0.02, 0.3, 0.4, 0.5 or 1 to 5, 6, 7, 8, 9 or 10 weight percent.

The present photoresist compositions typically comprise a solvent. Suitable solvents include, for example: glycol ethers such as 2-methoxyethyl ether (diglyme), ethylene glycol monomethyl ether, and propylene glycol monomethyl ether; propylene glycol monomethyl ether acetate; lactates such as methyl lactate and ethyl lactate; propionates such as methyl propionate, ethyl propionate, ethyl ethoxy propionate and methyl-2-hydroxy isobutyrate; Cellosolve esters such as methyl Cellosolve acetate; aromatic hydrocarbons such as toluene and xylene; and ketones such as acetone, methylethyl ketone, cyclohexanone and 2-heptanone. A blend of solvents such as a blend of two, three or more of the solvents described above also are suitable. The solvent is typically present in the composition in an amount of from 90 to 99 wt %, more typically from 95 to 98 wt %, based on the total weight of the photoresist composition.

The photoresist compositions can also include other optional materials. For example, the compositions can include one or more of actinic and contrast dyes, anti-striation agents, plasticizers, speed enhancers, sensitizers, and the like. Such optional additives if used are typically present in the composition in minor amounts such as from 0.1 to 10 wt % based on total solids of the photoresist composition.

The photoresists of the invention are generally prepared following known procedures. For example, a photoresist composition of the invention can be prepared by dissolving the components of the photoresist in a suitable solvent. The resin binder component of photoresists resists of the invention are typically used in an amount sufficient to render an exposed coating layer of the resist developable such as with an aqueous alkaline solution. More particularly, a resin binder will suitably comprise 50 to 90 weight percent of total solids of the resist. The photoactive component should be present in an amount sufficient to enable generation of a latent image in a coating layer of the resist. More specifically, the photoactive component will suitably be present in an amount of from 1 to 40 weight percent of total solids of a photoresist. Typically, lesser amounts of the photoactive component will be suitable for chemically amplified resists.

The desired total solids content of the present photoresist compositions will depend on factors such as the particular polymers in the composition, final layer thickness and exposure wavelength. Typically the solids content of the photoresist varies from 1 to 10 wt %, more typically from 2 to 5 wt %, based on the total weight of the photoresist composition.

Preferred negative-acting compositions of the invention comprise a mixture of materials that will cure, crosslink or harden upon exposure to acid, and a photoactive component of the invention. Particularly preferred negative acting compositions comprise a resin binder such as a phenolic resin, a crosslinker component and a photoactive component of the invention. Such compositions and the use thereof has been disclosed in European Patent Applications 0164248 and 0232972 and in U.S. Pat. No. 5,128,232 to Thackeray et al. Preferred phenolic resins for use as the resin binder component include novolaks and poly(vinylphenol)s such as those discussed above. Preferred crosslinkers include amine-based materials, including melamine, glycolurils, benzoguanamine-based materials and urea-based materials. Melamine-formaldehyde resins are generally most preferred. Such crosslinkers are commercially available, e.g. the melamine resins sold by American Cyanamid under the trade names Cymel 300, 301 and 303. Glycoluril resins are sold by American Cyanamid under trade names Cymel 1170, 1171, 1172, urea-based resins are sold under the trade names of Beetle 60, 65 and 80, and benzoguanamine resins are sold under the trade names Cymel 1123 and 1125.

The photoresists of the invention can be used in accordance with known procedures. Though the photoresists of the invention may be applied as a dry film, they are preferably applied on a substrate as a liquid coating composition, dried by heating to remove solvent preferably until the coating layer is tack free, exposed through a photomask to activating radiation, optionally post-exposure baked to create or enhance solubility differences between exposed and nonexposed regions of the resist coating layer, and then developed preferably with an aqueous alkaline developer to form a relief image. The substrate on which a resist of the invention is applied and processed suitably can be any substrate used in processes involving photoresists such as a microelectronic wafer. For example, the substrate can be a silicon, silicon dioxide or aluminum-aluminum oxide microelectronic wafer. Gallium arsenide, ceramic, quartz or copper substrates may also be employed. Substrates used for liquid crystal display and other flat panel display applications are also suitably employed, for example, glass substrates, indium tin oxide coated substrates and the like. A liquid coating resist composition may be applied by any standard means such as spinning, dipping or roller coating.

The exposure energy should be sufficient to effectively activate the photoactive component of the radiation sensitive system to produce a patterned image in the resist coating layer. Suitable exposure energies typically range from 1 to 300 mJ/cm$^2$. As discussed above, preferred exposure wavelengths include sub-200 nm such as 193 nm.

The photoresist layer (with overcoated barrier composition layer, if present) may be preferably exposed in an immersion lithography system, i.e. where the space between the exposure tool (particularly the projection lens) and the photoresist coated substrate is occupied by an immersion fluid, such as water or water mixed with one or more additives such as cesium sulfate which can provide a fluid of enhanced refractive index. Preferably the immersion fluid (for example, water) has been treated to avoid bubbles, for example water can be degassed to avoid nanobubbles.

References herein to "immersion exposing" or other similar term indicates that exposure is conducted with such a fluid layer (for example, water or water with additives) interposed between an exposure tool and the coated photoresist composition layer.

After exposure, a thermal treatment is typically employed for chemically-amplified photoresists. Suitable post-exposure bake temperatures are from about 50° C. or greater, more specifically from 50 to 140° C. For an acid-hardening negative-acting resist, a post-development bake may be employed if desired at temperatures of from 100 to 150° C. for several minutes or longer to further cure the relief image formed upon development. After development and any post-development cure, the substrate surface bared by development may then be selectively processed, for example chemically etching or plating substrate areas bared of photoresist in accordance with procedures known in the art. Suitable etchants include a hydrofluoric acid etching solution and a plasma gas etch such as an oxygen plasma etch.

The invention also provide methods for forming relief images of the photoresists of the invention, including methods for forming highly resolved patterned photoresist images (for example, a patterned line having essentially vertical sidewalls) of sub-quarter μm dimensions or less, such as sub-0.2 or sub-0.1 μm dimensions.

The invention further provides articles of manufacture comprising substrates such as a microelectronic wafer or a flat panel display substrate having coated thereon the photoresists and relief images of the invention.

EXAMPLES 1 AND 2 AND COMPARATIVE EXAMPLES 1 AND 2

Photoresist Preparation and Lithographic Processing

Four photoresists were formulated using the components shown below in Table 1 as weight percent based on 100% solids content, with the balance of the solids being the polymer.

TABLE 1

| Example | Polymer | PAG | Base | SLA | PGMEA (w/w of solvent) | HBM (w/w of solvent) | % solids |
|---|---|---|---|---|---|---|---|
| Comp. Ex. 1 | Polymer 1 (100) | PAG1 (10%) | Base 1 (0.902%) | PF656 (0.1%) | 50 | 50 | 4 |
| Comp. Ex. 2 | Polymer 1 (100) | PAG1 (10%) | Base 2 (1.029%) | PF656 (0.1%) | 50 | 50 | 4 |
| Ex. 1 | Polymer 1 (100) | PAG1 (10%) | Base 4 (1.182%) | PF656 (0.1%) | 50 | 50 | 4 |
| Ex. 2 | Polymer 1 (100) | PAG1 (10%) | Base 5 (1.049%) | PF656 (0.1%) | 50 | 50 | 4 |

Polymer 1: IAM/ECPMA/ODOTMA/a/HAMA (20/20/30/20/10) and has Mw of 8000.

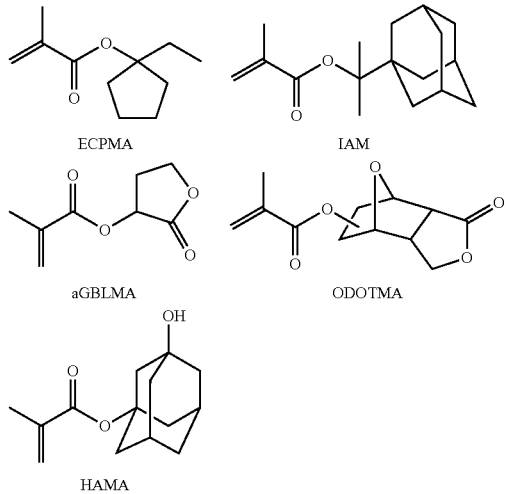

ECPMA IAM
aGBLMA ODOTMA
HAMA

PAG 1: triphenylsulfonium 1'-adamantanemethoxycarbonyl-2,2-difluoromethanesulfonate

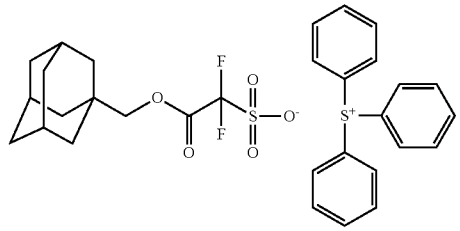 [SMILES: O=C(OCC12CC3CC(CC(C3)C1)C2)C(F)(F)S(=O)(=O)[O-] ; c1ccc([S+](c2ccccc2)c2ccccc2)cc1]

Comp. Base 1: N,N-diethyl-3-oxobutanamide

Comp. Base 2: N-t-butyloxycarbonyl-4-hydroxypiperidine

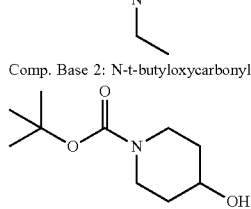

Base 8: N-(1,3-dihydroxy-2-(hydroxymethyl)propan-2-yl)pentanamide
Base 17: 2,4-dihydroxy-N-(3-hydroxypropyl)-3,3-dimethylbutanamide
Surface leveling agent (SLA): fluorinated (PF 656)

Lithography Process and Results

The formulated photoresists were spin coated using TEL ACT-8 (Tokyo Electron) coating track onto a 200 mm silicon wafer having as bottom antireflective coating (BARC) (AR™77, Dow Electronic Materials), and soft baked at 110° C. for 60 seconds, to form a resist film of about 100 nm in thickness. The photoresist layer was exposed using an ASML/1100, 0.75 NA stepper operating at 193 nm through a photomask with PSM feature size of 90 nm 1:1 Line/Space pattern, under Annular illumination with outer/inner sigma of 0.89/0.64 with focus offset/step 0.10/0.05. The exposed wafers were post-exposed baked (PEB) at 100° C. for 60 seconds. The coated wafers were next treated with a metal ion free base developer (0.26N aqueous tetramethylammonium hydroxide solution) to develop the photoresist layer. Line Width Roughness (LWR) was determined by processing the image captured by top-down scanning electron microscopy (SEM) using a Hitachi 9380 CD-SEM, operating at an accelerating voltage of 800 volts (V), probe current of 8.0 picoamperes (pA), using 200 K× magnification. LWR was measured over a 2 μm line length in steps of 40 nm, and reported as the average for the measured region. Results are shown in the following Table 2.

TABLE 2

| Examples | Eo | LWR |
|---|---|---|
| Comp. Ex. 1 | 8 | 13.5 |
| Comp. Ex. 2 | 8.4 | 12.79 |
| Ex. 1 | 7.6 | 11.3 |
| Ex. 2 | 6.2 | 9.8 |

In Table 2, Eo (Energy to clear is the exposure dose in mJ/cm2 of 193 wavelength radiation required to remove bulk film.

In Table 2, LWR (Line width Roughness) is defined as the length width over a range of spatial frequencies. The lower the LWR value, the smoother the line.

As can be seen from the above data, amide compounds with multiple hydroxyl groups of the invention provide improved lithographic performance as compared to other amide compounds that do not contain multiple hydroxyl groups.

What is claimed is:

1. A photoresist composition comprising:
   (a) a resin;
   (b) a photoacid generator compound; and
   (c) a non-polymeric amide compound that comprises i) an amide group, ii) two or more hydroxyl groups and iii) one or more cyano groups and/or one or more carboxyl group.

2. The photoresist composition of claim 1 wherein the amide compound contains a single amide moiety.

3. The photoresist composition of claim 1 wherein the amide compound corresponds to a structure of the following Formula (I):

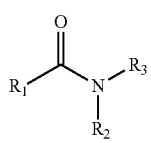

(I)

wherein R1, R2 and R3 are each independently hydrogen or a non-hydrogen substituent; and R1, R2 and R3 together comprise two or more hydroxyl groups.

4. The photoresist composition of claim 3 wherein R1 is a non-hydrogen substituent and at least one of R2 and R3 are non-hydrogen substituents.

5. The photoresist composition of claim 3 wherein R1 is optionally substituted alkyl, and R2 and R3 are independently hydrogen or optionally substituted alkyl.

6. The photoresist composition of claim 3 wherein R1, R2 and R3 are each the same or different optionally substituted alkyl.

7. The photoresist of claim 3 wherein 1) R1 and R2 are taken together to provide an optionally substituted lactam group and/or 2) R2 and R3 are taken together to provide a ring structure.

8. The photoresist composition of claim 3 wherein R1 is $(C_1-C_{30})$alkyl optionally substituted with a hydroxyl group, and R2 and R3 are independently hydrogen or a $(C_1-C_{30})$ alkyl optionally substituted with a hydroxyl group, and R1, R2 and R3 together comprise two or more hydroxyl groups.

9. The photoresist composition of claim 1 wherein the amide compound comprises three or more hydroxyl groups.

10. The photoresist composition of claim 1 wherein the amide compound comprises at least one primary hydroxyl group.

11. The photoresist composition of claim 1 wherein the amide compound comprises at least one secondary hydroxyl group.

12. The photoresist composition of claim 1 wherein the amide compound comprises one or more carboxyl groups.

13. The photoresist composition of claim 1 wherein the amide compound has a molecular weight of about 2500 or less.

14. The photoresist composition of claim 1 wherein the amide compound has a molecular weight of about 1500 or less.

15. The photoresist composition of claim 1 wherein the amide compound has a molecular weight of about 500 or less.

16. A method for forming a photoresist relief image comprising:
   (a) applying a coating layer of a photoresist composition of claim 1 on a substrate;
   (b) exposing the photoresist coating layer to patterned activating radiation and developing the exposed photoresist layer to provide a relief image.

17. The method of claim 16 wherein the photoresist coating layer is immersion exposed.

18. A method for forming a photoresist relief image comprising:
   (a) applying on a substrate a coating layer of a photoresist composition that comprises:
      (i) a resin;
      (ii) a photoacid generator compound; and
      (iii) an amide compound that corresponds to a structure of the following Formula (I):

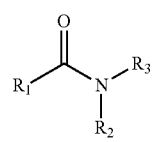

(I)

wherein R1 is $(C_1-C_{30})$alkyl optionally substituted with a hydroxyl group, and R2 and R3 are independently hydrogen or a $(C_1-C_{30})$alkyl optionally substituted with a hydroxyl group, and R1, R2 and R3 together comprise two or more hydroxyl groups, and wherein 1) R1 and R2 are taken together to provide an optionally substituted lactam group and/or 2) R2 and R3 are taken together to provide a ring structure, (b) exposing the photoresist coating layer to patterned activating radiation and developing the exposed photoresist layer to provide a relief image.

* * * * *